United States Patent [19]

Kumonaka et al.

[11] Patent Number: 4,780,560

[45] Date of Patent: Oct. 25, 1988

[54] NITRATE DERIVATIVES AND VASODILATORS CONTAINING THE SAME

[75] Inventors: Takahiro Kumonaka, Kawasaki; Shigeru Taguchi, Tama; Yasushi Suwabe, Kawasaki; Toshio Wakabayashi, Tama, all of Japan

[73] Assignee: Terumo Corporation, Tokyo, Japan

[21] Appl. No.: 20,704

[22] Filed: Mar. 2, 1987

[30] Foreign Application Priority Data

Mar. 5, 1986 [JP] Japan ................................. 61-48158

[51] Int. Cl.$^4$ ............................................. C07C 77/02
[52] U.S. Cl. ................................... 558/482; 558/483; 514/929
[58] Field of Search ...................... 558/480, 482, 483; 514/622, 617, 929; 568/927

[56] References Cited

U.S. PATENT DOCUMENTS 3,659,014  4/1972  Bayssat et al. .

FOREIGN PATENT DOCUMENTS 57-32255  2/1982  Japan .
906319  9/1962  United Kingdom .

Primary Examiner—John F. Terapane
Assistant Examiner—Susan Wolffe
Attorney, Agent, or Firm—Cushman, Darby & Cushman

[57] ABSTRACT

Novel nitrate derivatives are disclosed. As examples of said nitrate derivative are described N-($\beta$-hydroxyethyl)-5-(3,4,5-trimethoxyphenyl)2,4-pentadienoic acid amide nitrate, N-($\beta$-hydroxyethyl)-3,4,5-trimethoxycinnamic acid amide nitrate and the like. These nitrate derivatives are useful as vasodilators.

6 Claims, No Drawings

NITRATE DERIVATIVES AND VASODILATORS CONTAINING THE SAME

BACKGROUND OF THE INVENTION (1) Field of the Invention

The present invention relates to nitrate derivatives and vasodilators containing the same. The nitrate derivatives provided by the invention are novel compounds which possess potent vasodilating activities. Therefore, they are useful for vascular disturbances to be treated by increasing blood flow such as coronary vascular disturbances, cerebral vascular disturbances and peripheral vascular diseases.

2. Description of Prior Arts

Vascular disturbances associated with sequelae of diseases such as myocardial infarction and cerebral thrombosis have become a greater part of adult diseases in recent years, and development of drugs for effectively preventing such disturbances is highly desirable.

Heretofore, a variety of vasodilators including 3,4,5-trimethoxycinnamate derivatives have been developed. However, they are not necessarily satisfactory in efficacy for pharmaceutical use.

SUMMARY OF THE INVENTION

A variety of nitrate derivatives were synthesized by us employing 5-(3,4,5-trimethoxyphenyl)-2,4-pentadienoic acid and their pharmacological activities were extensively investigated. As a result, we have found that the compounds according to the present invention possess high vasodilating activities.

Accordingly, it is an object of the invention to provide nitrate derivatives represented by the general formula (I)

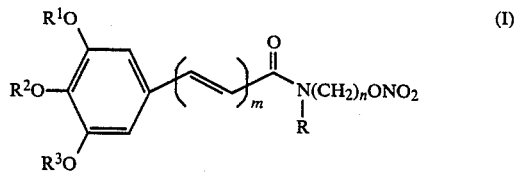

wherein $R^1$, $R^2$ and $R^3$ which may be the same or different represent a lower alkyl group, R represents a hydrogen atom or a lower alkyl group, m represents an integer of 1 or 2 and n represents an integer from 2 to 5.

A further object of the invention is to provide vasodilators containing a nitrate derivative represented by the general formula (I).

DETAILED DESCRIPTION OF THE INVENTION

In the definition of substituents in the formula (I) as mentioned above, the lower alkyl group means straight or branched alkyl groups containing from 1 to 5 carbon atoms and is preferably methyl, ethyl, isopropyl, propyl, butyl, isobutyl, amyl, isoamyl or the like.

It is preferable that $R^1$, $R^2$ and $R^3$ in the formula (I) as mentioned above are the same lower alkyl groups, particularly methyl groups.

As preferred examples of the nitrate derivative of the formula (I) are mentioned:

N-(β-Hydroxyethyl)-5-(3,4,5-trimethoxyphenyl)-2,4-pentadienoic acid amide nitrate, N-(γ-hydroxypropyl)-5-(3,4,5-trimethoxyphenyl)-2,4-pentadienoic acid amide nitrate, N-(δ-hydroxybutyl)-5-(3,4,5-trimethoxyphenyl)-2,4-pentadienoic acid amide nitrate, N-(β-hydroxyethyl)-5-(3,4,5-triethoxyphenyl)-2,4-pentadienoic acid amide nitrate, N-(β-hydroxyethyl)-3,4,5-trimethoxycinnamic acid amide nitrate, N-(γ-hydroxypropyl)-3,4,5-trimethoxycinnamic acid amide nitrate, N-(δ-hydroxybutyl)-3,4,5-trimethoxycinnamic acid amide nitrate, and N-(β-hydroxyethyl)-3,4,5-triethoxycinnamic acid amide nitrate.

The nitrate derivatives represented by the formula (I) as mentioned above are prepared by reacting a reactive derivative of a carboxylic acid having the formula (II)

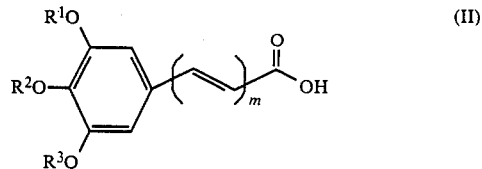

wherein $R^1$, $R^2$, $R^3$ and m have the same meaning as defined above with an amine derivative having the formula (III)

wherein R and n have the same meaning as defined above.

As the reactive derivative of the above-mentioned carboxylic acid of the formula (II) are mentioned halides (for example, chloride), anhydride, mixed acid anhydrides (for example, mixed anhydride with formic acid), active amides (for example, thiazolidinethionamide) and the like of said carboxylic acid.

The reaction is carried out by contacting a reactive derivative of the above-mentioned carboxylic acid (II) with the amine derivative (III) in the atmosphere of an inert gas in the presence of an organic solvent preferred as the organic solvent are tetrahydrofuran, dioxane ether, methylene chloride, chloroform, ethyl acetate, etc. It is preferred to carry out the reaction in the presence of an acid-binding agent such as triethylamine, tripropylamine, tributylamine, etc. The reaction temperature and time are 0°–100° C. and 1–20 hours, respectively. After completion of the reaction, the desired reaction product is isolated from the reaction mixture and purified according to conventional procedures. For example, the desired product is obtained by extracting the reaction mixture with an appropriate organic solvent such as methylene chloride, removing the solvent from the extract by distillation and subjecting the residue to column chromatography.

The nitrate derivatives of the invention are useful as vasodilators valuable for diseases such as coronary vascular disturbances, cerebral vascular disturbances and peripheral vascular disturbances. In general, the dosage is in the range from 3 to 100 mg per day in adults, which may be divided into 1 to 3 doses as needed. Whereas the administration is desirably by oral route, intravenous injection can be applied.

The nitrate derivatives of the invention are blended with pharmaceutical carriers or recipients by a conventional method to form pharmaceutical preparations such as tablets, powders, capsules and granules. As examples of the carrier of recipient are mentioned calcium carbonate, calcium phosphate, starch, sucrose, lactose, talc, magnesium stearate and the like. The nitrate ester derivatives of the invention can als be formulated into liquid preparations such as oily suspension, syrup and injection.

The invention will be described in more details with reference to examples as well as results of the general test to demonstrate the vasodilating activity and the acute toxicity test.

EXAMPLE 1

To a solution of 4.215 g of monoethanolamine nitrate nitrate and 5.215 ml of triethylamine in 100 ml of water was added in the atmosphere of argon, a solution of 9.110 g of 5-(3,4,5-trimethoxyphenyl)-2,4-pentadienoic acid thiazolidine-2-thionamide in 100 ml of tetrahydrofuran at room temperature. The mixture was reacted overnight at room temperature followed by removal of the tetrahydrofuran by distillation under reduced pressure. To the residue was added 80 ml of 0.5 N aqueous solution of sodium hydroxide, and the mixture was extracted three times with methylene chloride. The organic layer was washed with water and dried over anhydrous sodium sulfate. The solvent was then removed by distillation under reduced pressure to yield 9.705 g of residue from the extract. The residue was subjected to column chromatography on silica gel. There was obtained 5.268 g of N-($\beta$-hydroxyethyl)-5-(3,4,5-trimethoxyphenyl)-2,4-pentadienoic acid amide nitrate from the benzene-ethyl acetate (4:1) eluate fraction. Physicochemical data of the product support the structure of the formula (IV) below:

IR $\nu_{max(cm-1)}^{CHCl_3}$: 3445, 1670, 1640, 1620, 1580, 1505, 1275.

$^1$N-NMR(CDCl$_3$): $\delta$(ppm): 3.83 (9H,S), 4.57 (2H, t, J=5.5 Hz), 6.02 (2H, d, J=15 Hz).

MS(m/e) Field emission (FDMS): 352 (molecular ion peak), 289 (de-HNO$_3$ peak).

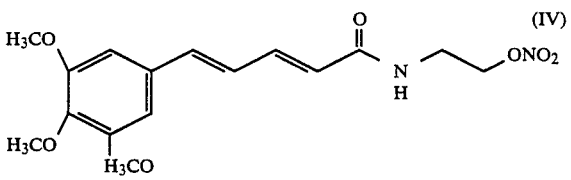

(IV)

EXAMPLE 2

To a solution of 2.245 g of monoethanolamine nitrate nitrate and 2.80 ml of triethylamine in 75 ml of methanol was added in the atmosphere of argon, 4.500 g of 3,4,5-trimethoxycinnamic acid thiazolidine-2-thionamide in 125 ml of chloroform at room temperature. The mixture was reacted at room temperature for 8.5 hours, and to the reaction mixture was added 100 ml of 0.5 N aqueous solution of sodium hydroxide. The mixture was extracted three times with chloroform. The organic layer was washed with water and dried over anhydrous sodium sulfate. The solvent was removed by distillation under reduced pressure to yield 4.530 g of residue. The residue was subjected to column chromoatography on silica gel. There was obtained 3.416 g of N-($\beta$-hydroxyethyl)-3,4,5-trimethoxycinnamic acid amide nitrate.

Physicochemical data of the produce support the structure of the formula (V) below.

IR $\nu_{max(cm-1)}^{CHCl_3}$: 3450, 1675, 1640, 1585, 1510, 1280.

$^1$H-NMR(CDCl$_3$): $\delta$(ppm): 3.77 (6H,S), 3.82 (3H,S), 4.57 (2H, t, J=5.5 Hz) 6.35 (1H, d, J=15 Hz), 6.63 (2H, S), 7.50 (1H, d, J=15 Hz).

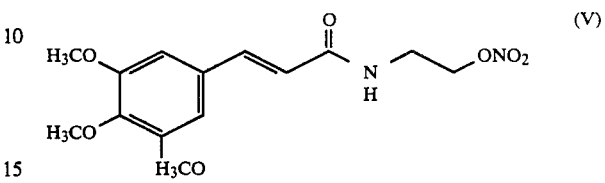

(V)

TEST EXAMPLE (Vasodiating activity)

Hybrid adult dogs (weighting about 10 kg) were anesthetized with sodium pentobarbital (at a dose of 32.4 mg/kg body weight, i.v.), subjected under artificial respiration to detachment of the right vertebral artery and the coronary artery and equipped with non-blooding probes to measure coronary blood flow and vertebral blood flow. A suspension of the compounds produced in the above examples in 0.5% HCO 60 solution was administered through the lateroradial dermal vein. Then, the vasodilating activity was demonstrated by increases in coronary blood flow and vertebral blood flow. Increases in coronary blood flow and vertebral blood flow by administration of the above-mentioned compounds as compared with those prior to the administration are shown in Table 1 with reference to typical examples. As a control drug was employed Cinnepazied (1-[(1-pyrrolidinylcarbonyl)methyl]-4-(3,4,5-trimethyoxycinnamoyl)piperazine).

TABLE 1

| | | | Vasodilating activities | |
| --- | --- | --- | --- | --- |
| | | | Increase in blood flow ($\Delta\%$ ± SE) | |
| Test compound | Dose (mg/kg, i.v.) | Number of Animals | Coronary artery | Vertebral artery |
| Example 1 | 0.3 | 3 | 3.6 ± 0.2 | 50.0 ± 2.4 |
| | 1.0 | 3 | 28.6 ± 1.9 | 83.3 ± 7.5 |
| Example 2 | 0.3 | 3 | 3.8 ± 0.5 | 35.0 ± 1.7 |
| | 1.0 | 3 | 22.9 ± 1.5 | 58.3 ± 5.3 |
| Cinnepazid (Control drug) | 0.3 | 3 | 2.1 ± 0.8 | 1.5 ± 0.4 |
| | 1.0 | 3 | 10.0 ± 0.5 | 5.6 ± 0.2 |

(Acute toxicity)

An acute toxicity test was run in ICR male mice (5-week old) by oral administration. LD$_{50}$'s of the nitrate ester derivatives of the invention were 300 mg/kg body weight or higher with any compound tested thereby demonstrated higher safety as compared with effective dose.

According to the present invention, there are provided novel nitrate derivatives and vasodilators containing the same.

The above-mentioned compounds of the invention possess vasodilating activities so that they can effectively be used as curing or preventing agents for vascular disturbances such as cerebral thrombosis, myocardial infarction and sequelae of cerebral thrombosis.

What is claimed is:

1. A nitrate derivative represented by the general formula

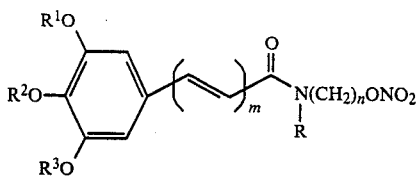

wherein $R^1$, $R^2$ and $R^3$ which may be the same or different represent a lower alkyl group, R represents a hydrogen atom or a lower alkyl group, m represents an integer of 1 or 2 and n represents an integer from 2 to 5.

2. A nitrate derivative according to claim 1 wherein $R^1$, $R^2$, and $R^3$ are the same lower alkyl groups.

3. A nitrate derivative according to claim 2 wherein $R^1$, $R^2$ and $R^3$ are methyl groups.

4. A vasodilator composition comprising a nitrate derivative according to claim 1 as the active ingredient and a pharmaceutically acceptable carrier.

5. A vasodilating method which comprises administering to mammals an effective dose of the nitrate derivative according to claim 1.

6. The vasodilating method according to claim 5 wherein the dosage is 3–100 mg per day in adults.

* * * * *